(12) United States Patent
Song et al.

(10) Patent No.: US 7,060,673 B2
(45) Date of Patent: Jun. 13, 2006

(54) FUSION PEPTIDE OF HUMAN PARATHYROID HORMONE DERIVED PEPTIDE AND TAT PEPTIDE, PREPARATION THEREOF, AND SKIN SLIMMING COSMETIC COMPOSITION COMPRISING THE SAME

(75) Inventors: Young-Sook Song, Taejeon (KR);
Nae-Gyu Kang, Taejeon (KR);
Sun-Gyoo Park, Taejeon (KR);
Wan-Goo Cho, Taejeon (KR);
Yong-Hwa Lee, Taejeon (KR);
Jun-Man Lim, Taejeon (KR);
Hye-Jung Min, Taejeon (KR);
Min-Youl Chang, Taejeon (KR);
Seh-Hoon Kang, Taejeon (KR)

(73) Assignee: LG Household and Health Care Ltd., Seoul (KR)

( * ) Notice: Subject to any disclaimer, the term of this patent is extended or adjusted under 35 U.S.C. 154(b) by 363 days.

(21) Appl. No.: 10/296,033

(22) PCT Filed: May 6, 2002

(86) PCT No.: PCT/KR02/00835

§ 371 (c)(1),
(2), (4) Date: Nov. 20, 2002

(87) PCT Pub. No.: WO03/035697

PCT Pub. Date: May 1, 2003

(65) Prior Publication Data

US 2005/0048629 A1     Mar. 3, 2005

(30) Foreign Application Priority Data

Sep. 27, 2001 (KR) ............................ 2001-0060245
Mar. 15, 2002 (KR) ............................ 2002-0014062

(51) Int. Cl.
*A61K 38/00* (2006.01)
*C12P 21/04* (2006.01)

(52) U.S. Cl. .............................. 514/2; 514/12; 514/15; 530/300; 530/334; 530/344; 435/69.1; 435/69.7

(58) Field of Classification Search ............... 435/69.7, 435/69.1; 514/2, 12, 15; 530/300, 334, 530/344
See application file for complete search history.

(56) References Cited

FOREIGN PATENT DOCUMENTS

WO     WO00/40611    *   7/2000

OTHER PUBLICATIONS

Schwartze et al., Science vol. 285, No. 5433, pp. 1569-1572 (Sep. 1999).*
Vivies et al., J. Biol. Chem. 272 (25), 16010-16017 (Jun. 1997).*
Futake et al., J. Biol. Chem. 276 (8), 5836-5840 (Feb. 2001).*

* cited by examiner

*Primary Examiner*—Kathleen M. Kerr
*Assistant Examiner*—Chih-Min Kam
(74) *Attorney, Agent, or Firm*—Alston & Bird LLP

(57) ABSTRACT

The present invention relates to a fusion peptide wherein a self cell-penetrating Tat peptide having a self penetrating signal is bound to a human parathyroid hormone-derived peptide, a preparation thereof, and a skin slimming cosmetic composition comprising the same. Since the fusion peptide wherein the Tat peptide is bound to the human parathyroid hormone-derived peptide has high stability and superior skin absorption, the present invention provides a skin slimming agent having superior lipolysis effects and improved durability of the effects.

3 Claims, No Drawings

FUSION PEPTIDE OF HUMAN PARATHYROID HORMONE DERIVED PEPTIDE AND TAT PEPTIDE, PREPARATION THEREOF, AND SKIN SLIMMING COSMETIC COMPOSITION COMPRISING THE SAME

This application is a 371 of PCT/KR02/00835, filed May 6, 2002, which claims foreign priority benefits of Republic of Korea Application No. 2001-0060245, filed Sep. 27, 2001, and Republic of Korea Application No. 2002-0014062, filed Mar. 15, 2002.

BACKGROUND OF THE INVENTION (a) Field of the Invention

The present invention relates to a fusion peptide wherein a self cell-penetrating Tat peptide (transactivator of transcription peptide) is bound to a human parathyroid hormone-derived peptide, and a skin slimming cosmetic composition comprising the same.

(b) Description of the Related Art

Human parathyroid hormone (hPTH), which is a peptide hormone consisting of 84 amino acids produced in the parathyroid of a human body, functions for controlling homeostasis of calcium in the kidneys and bones, and administration of a small amount thereof influences metabolism or bone formation [Morel F., et. al., Academic press, 1983 39, 271; Norman, A. W. et. al., Endocrinal Rev., 1982 3, 336]. In addition, parathyroid hormone functions for calcium control, blood vessel contraction, lymph flow, adrenalin control, etc., and promotes lipolysis. Particularly, it has been reported that a peptide consisting of amino acids 1 to 34 of the amino acid sequence of parathyroid hormone acts on human adipocytes to promote lipolysis [Werner S. et. al., Horm. Metab. Res., 1973 5, 292, Tanigushi A., et. al., J. Lip. Res., 1987 28, 490]. It was expected that a parathyroid hormone-derived peptide is effective for slimming from the report that if a parathyroid hormone acts on an adipocyte recipient, lipolysis will be promoted by a control mechanism of promoting cAMP production. Therefore, as a result of synthesizing various peptides and screening, it has been clarified that peptides of amino sequences 9 to 19, 12 to 16, and 12 to 14 of parathyroid hormone are effective for slimming (France Patent Application No. 2788058, PCT Laid-open Publication No. WO 00/40611, Richard L., et. al., S.P.C. 2001, Dec. 30). However, these peptides have weak skin absorbency due to water-solubility and thus it is largely difficult to anticipate lipolysis effects. Therefore, there is an urgent need for development of a novel skin slimming agent having increased absorbency through skin and thus maximizing slimming effects in a living body.

As one method for increasing skin absorbency of these peptide slimming agents, a method of grafting a long chain fatty acid such as palmitic acid on a peptide has been suggested in order to increase fat solubility of the peptide (France Patent Application No. 2788058, PCT Laid-open Publication No. WO 00/40611), but the absorbency increase was not largely improved.

Accordingly, there is a need for development of a novel skin slimming agent that does not cause irritation on skin and that has increased absorbency through skin, improved stability, and maximized slimming effects in living bodies.

SUMMARY OF THE INVENTION

In order to solve these problems of the prior art, it is an object of the present invention to provide a fusion peptide wherein a Tat peptide having a self cell-penetration property is bound to a human parathyroid hormone-derived peptide, which does not cause irritation, easily and safely penetrates into the integument and endothelium, does not cause skin disease, and has superior lipolysis effects continuously.

It is another object of the present invention to provide a method for preparing a fusion peptide wherein a self cell-penetrating Tat peptide is bound to a human parathyroid hormone-derived peptide.

It is another object of the present invention to provide a skin slimming cosmetic composition comprising a fusion peptide wherein a self cell-penetrating Tat peptide is bound to a human parathyroid hormone-derived peptide, having superior cell-penetration properties and lipolysis effects, and is durable.

In order to achieve these objects, the present invention provides a fusion peptide wherein a Tat peptide having a self cell-penetration property is bound to a human parathyroid hormone-derived peptide (Tat-hPTHDP):

[Chemical Formula 1]

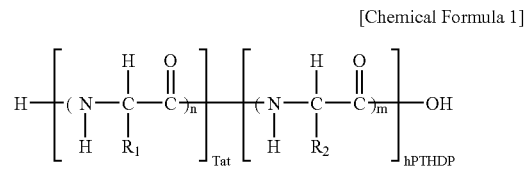

wherein $[\ ]_{Tat}$ is a Tat peptide having a self cell-penetration property; $R_1$ is one or more kinds selected from a group consisting of side chains of glutamine, lysine, arginine, and glycine; n is an integer of 4 to 12;

$[\ ]_{hPTHDP}$ is a peptide derived from human parathyroid hormone consisting of continuous 3 to 34 amino acids of the peptide shown in Sequence No. 1; $R_2$ is a side chain of amino acids comprising the peptide; and m is an integer of 3 to 34.

DETAILED DESCRIPTION AND THE PREFERRED EMBODIMENTS

The present invention will now be explained in detail.

The present invention provides a fusion peptide wherein a Tat peptide having a self cell-penetration property is bound to a peptide derived from human parathyroid hormone, represented by the following Chemical Formula 1 (Tat-hPTHDP):

[Chemical Formula 1]

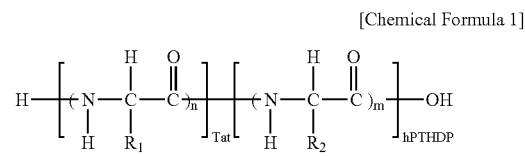

In the formula, $[\ ]_{Tat}$ is a Tat peptide having a self cell-penetration property; the Chemical Formula in $(\ )_n$ represents an amino acid sequence; $R_1$ is one or more kinds selected from a group consisting of side chains of glutamine, lysine, arginine, and glycine; and n is an integer of 4 to 12.

Further, [ ]$_{hPTHDP}$ is a peptide derived from human parathyroid hormone consisting of continuous 3 to 34 amino acids of the peptide shown in Sequence No. 1 (m=3~34), and preferably a peptide consisting of 3 to 11 amino acids of the peptide shown in Sequence No. 1 (m=3~11), for example, a peptide comprising a whole or a part of a peptide of Sequence No. 2 or Sequence No. 3, and more preferably, a peptide of Sequence No. 3 (m=6), a peptide of Sequence No. 5 (m=5), or a peptide of Sequence No. 6 (m=3); R$_2$ is a side chain of an amino acid of the peptide; and m is an integer of 3 to 34.

The sequence of amino acids 1 to 34 of the human parathyroid hormone is as follows, and it is also shown in Sequence No. 1 (SEQ ID NO. 1):

```
N-Ser-Val-Ser-Glu-Ile-Gln-Leu-Met-His-Asn-

Leu-Gly-Lys-His-Leu-Asn-Ser-Met-Glu-Arg-

Val-Glu-Trp-Leu-Arg-Lys-Lys-Leu-Gln-Asp-

Val-His-Asn-Phe-C.
```

A peptide derived from human parathyroid hormone (hPTHDP) used in the present invention is represented by the following Chemical Formula 2:

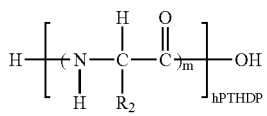

[Chemical Formula 2]

A peptide derived from human parathyroid hormone is a peptide consisting of 3 to 34 amino acids of the peptide shown in Sequence No.1 (m=3~34), preferably a peptide consisting of 3 to 11 amino acids of the peptide shown in Sequence No. 1 (m=3~11), for example a peptide comprising a whole or a part of a peptide of Sequence No. 2 or 3, and more preferably, a peptide of Sequence No. 3 (m=6), a peptide of Sequence No. 5 (m=5), or a peptide of Sequence No. 6 (m=3); R$_2$ is a side chain of the peptide; and m is an integer of 3 to 34.

More specifically, the peptide derived from human parathyroid hormone comprises a whole or a part of a peptide of Sequence No. 1; a whole or a part of a peptide of amino acids 1 to 10, Sequence No. 2 (hPTH 1–10, Ser-Val-Ser-Vlu-Ile-Gln-Leu-Met-His-Asn) (SEQ ID NO. 2); a peptide of amino acids 9 to 19, Sequence No. 3 (hPTH 9–19, His-Asn-Leu-Gly-Lys-His-Leu-Asn-Ser-Met-Glu) (SEQ ID NO. 3); a peptide of amino acids ito 6, Sequence No. 4 (hPTH 1–6, Ser-Val-Ser-Glu-Ile-Gln) (SEQ ID NO. 4); a peptide of amino acids 12 to 16, Sequence No. 5 (hPTH 12–16, Gly-Lys-His-Leu-Asn) (SEQ ID NO. 5): or a peptide of amino acids 12 to 14, Sequence No. 6 (hPTH 12–14, Gly-Lys-His) (SEQ ID NO. 6).

Recently, according to the fact that various human body diseases are due to abnormal activities of cell proteins, development of materials capable of treating fatal human body disease by controlling activities of these proteins has attracted worldwide attention. However, peptide and protein, despite having superior selectivity and usefulness for physical action to other compounds, are difficult to practically use as effective drug delivery means because they are difficult to directly deliver inside a cell.

In order to solve these problems, a recent protein penetration technology for effectively penetrating various bio-functioning proteins into cells has been used to directly and effectively deliver or absorb material required for human body disease treatment. Representative protein penetration technology uses a property of the Tat peptide, a kind of protein of the Human Immunodeficiency Virus type-1 (HIV) having self-penetration, of spontaneously passing through a cell membrane to easily penetrate and be transported into the cell. Such function appears due to the property of the protein transduction domain that is a middle region of the Tat peptide sequence, and the exact mechanism has not yet been clarified (Frankel, A. D. and Pabo, C. O. (1998) Cell 55, 1189–1193. Green, M. and Loewenstein, P. M. (1988) Cell 55, 1179–1188, Ma. M. and Nath, A. (1997) J. Virol. 71, 2495–2499. Vives, E., Brodin, P. and Lebleu, B. (1997) J. Biol. Chem. 272, 16010–16017.)

The present inventors, as a result of closely observing the cell-penetration property of the Tat peptide, covalently bonded skin-activating ingredients such as a human parathyroid hormone-derived peptide to a Tat peptide having a self penetration signal to directly and effectively penetrate the fusion peptide into cells inside skin, and thus completed the present invention.

"Self cell-penetrating Tat peptide" used herein means the Tat peptide itself or a peptide derived therefrom, and the Tat peptide or a peptide derived therefrom means a peptide having the cell-penetration property alone or in combination with a material bound thereto.

Specifically, the Tat peptide of HIV Type-i (human immunodeficiency virus) has a main feature of having a signal for opening the lipid barrier to be penetrated by the peptide sequence region in the N-terminal of the total protein, and the sequence is as follows, and is also shown in Sequence No. 7:

```
                                    (SEQ ID NO.7)
Arg-Lys-Lys-Arg-Arg-Gln-Arg-Arg-  (or RKKRRQRRR).

Arg
```

The self cell-penetrataing Tat peptide can be bound to the human parathyroid hormone-derived peptide by esterification with a carboxylic group through reaction with alcohol, because amino acids comprising the Tat peptide such as lysine (hereinafter referred to as Lys or K), arginine (Arg or R), glutamine (Gln or Q), etc. have amine groups and carboxy groups. Representative self cell-penetrating Tat peptides (n=9) are a Tat peptide of Sequence No. 7 (Arg-Lys-Lys-Arg-Arg-Gln-Arg-Arg-Arg or RKKRRQRRR) (SEQ ID NO. 7, a Tat peptide of Sequence No. 8 (Lys-Lys-Lys-Lys-Lys-Lys-Lys-Lys or KKKKKKKK) (SEQ ID NO. 8), a peptide of Sequence No. 9 (Arg-Arg-Arg-Arg-Arg-Arg-Arg-Arg or RRRRRRRRR) (SEQ ID NO. 9), etc., and they can be bound to hPTHDP by condensation.

The self cell-penetrating Tat peptide is represented by the following Chemical Formula 3:

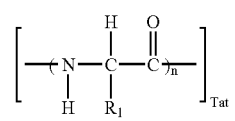

[Chemical Formula 3]

In the formula, $R_1$ is one or more kinds of substituents selected from a group consisting of side chains of glutamine (Gln), lysine (Lys), arginine (Arg), and glycine (Gly). The Tat peptide is a peptide consisting of 4 to 12 amino acids, and more preferably a peptide consisting of one or more kinds of amino acids selected from a group consisting of lysine and arginine. In addition, n is an integer of 4 to 12, preferably 8 to 10, and most preferably n is 9.

The present invention provides a method for preparing a fusion peptide wherein a self cell-penetrating Tat peptide is bound to a peptide derived from human parathyroid hormone (hPTHDP).

More specifically, the Tat-hPTHDP fusion peptide of the present invention can be prepared by the following methods.

First is a biological method using a recombinant expression vector, which is a method for preparing a Tat-HPTDP fusion peptide comprising the steps of (a) cloning a Tat gene of HIV-1 by PCR (polymer chain reaction) of the N-terminal with a self penetration signal region from pSVC21, an expression vector comprising the HIV-1 Tat gene, in a pET vector, a protein expression vector comprising a 6 His tag to prepare a vector capable of expressing a fusion protein; and (b) mass-expressing recombinant His-Tat-hPTHDP peptide in E. coli using the pET-Tat expression vector, then separating and purifying.

Second is a method for preparing a Tat-hPTHDP fusion peptide comprising the steps of integrating a target protein, for example catalase or superoxide dismutase (SOD), etc. into a pET-Tat-hPTHDP expression vector to mass-express His-Tat-hPTHDP fusion protein, then separating and purifying.

Third is a method for synthesizing a pure Tat-hPTHDP fusion peptide using an organosynthesizer for peptide synthesis. The method is Merrifield solid-phase peptide synthesis (J. Am. Chem. Soc. 85, 2149–2154(1963)), and the Tat-hPTHDP fusion protein is synthesized by condensation of the C-terminal of amino acid of the Tat-hPTHDP fusion peptide comprising a Tat peptide having one or more kinds of amino acids selected from a group consisting of Gln, Lys, Arg, and Gly, and monomers with N-terminal reactivity using a peptide synthesizer (Model 431A from ABI Company).

Solid phase synthesis starts by coupling an α-amino protected amino acid to an appropriate resin from an amino acid of a carboxy terminal. The α-amino protected amino acid is coupled to a hydroxy methyl resin or a chloro methylated resin through an ester bond. As an α-amino protecting group, Fmoc (9-fluorenyl methoxycarbonyl) or Boc (t-butyloxycarbonyl) is used, and Fmoc-protected amino acid is purchased from Pharmacia Company or Calbiochem Company. For examples of an amino acid having a reactive amino acid residue, an amino group of Arg residue or a reactive residue of Gly, Lys, or Gln is used; and Fmoc-amino acid protected with an appropriate group such as trityl (Trt), 4-methoxy-2,3-trimethylbenzene sulfunyl (MRT), tert-butyl (t-Bu) is used. Peptide is synthesized by sequentially coupling an α-amino protected amino acid to an amino terminal of a peptide chain attached to a solid support resin after activation. After synthesis, the peptide is cut from the resin, and the protecting group is removed with a reagent such as trifluoroacetic acid (TPA). The peptide is separated from the TFA solution by filtration, centrifugation, or extraction with diethylether, and it can be purified by high performance liquid chromatography (HPLC) or other methods.

The Tat-hPTHDP fusion peptide represented by the Chemical Formula 1 prepared according to the present invention can be used as a skin slimming agent having superior chemical stability, and durable lipolysis effects, and safety. A detailed activity evaluation thereof will be described in Examples.

The present invention provides a skin slimming cosmetic composition comprising a compound represented by the Chemical Formula 1.

The composition of the present invention comprises 0.000001 to 5.0 wt% of the compound represented by the Chemical Formula 1. If the contents are less than 0.000001 wt %, substantial slimming effects cannot be expected, and if the contents exceed 5.0 wt %, the compound would have a bad influence on stability of the product and the preparation form.

Kinds of applicable cosmetics are not specially limited, and common cosmetic forms can be applied. For examples, the composition of the present invention can be prepared in the form of external ointment, toner, lotion, nutrition cream, massage cream, essence, pack, emulsion, oil gel, etc. The external ointment comprises 50.0 to 97.0 wt % of Vaseline and 0.1 to 5.0 wt % of polyoxyethyleneoleyl-ether phosphate in addition to the compound represented by the Chemical Formula 1, and the toner comprises 1.0 to 10.0 wt % of polyalcohol such as propylene glycol, glycerine, etc. and 0.05 to 2.0 wt % of a surfactant such as polyethyleneoleylether, polyoxyethylene hardened castor oil, etc. The lotion and nutrition cream comprise 5.0 to 20.0 wt % of oil such as squalene, Vaseline, and octyldodecanol, and 3.0 to 15.0 wt % of waxy ingredients such as cetanol, stearylalcohol, paraffin, etc. in addition to the active ingredient of the compound represented by the Chemical Formula 1, and the essence comprises 5.0 to 3.0 wt % of polyalcohol such as glycerine, propyleneglycol, etc. The massage cream comprises 30.0 to 70.0 wt % of oil such as flow paraffin, Vaseline, isononylisononanoate, etc. in addition to the active ingredient of the compound of Chemical Formula 1, and the pack is prepared in the form of a peel-off pack comprising 5.0 to 20.0 wt % of polyvinylalcohol or a wash-off pack comprising common emulsifying cosmetics and 5.0 to 30.0 wt % of a pigment such as kaolin, talc, zinc oxide, titan dioxide, etc.

In addition, it is possible to mix ingredients commonly used in general skin cosmetics such as an oily substance, water, surfactant, moisturizer, low alcohol, thickener, chelating agent, pigment, antiseptic, perfume, etc. with the skin slimming cosmetic composition comprising the compound represented by the Chemical Formula 1 of the present invention, in an appropriate amount.

A transdermal absorption test, a skin stimulation test, a lipolysis effects test, and a slimming effects test were carried out in order to confirm physical activities of the compound of the present invention, and as a result, the compound of the present invention has been proven to have superior transdermal absorbency, and superior lipolysis and slimming effects. Since the compound of the present invention does not cause irritation and has superior activity and skin absorption and thus has superior slimming effects, it can be used in any form of cosmetics such as cream, lotion, gel, etc.

The present invention will be explained in more detail with reference to the following Examples. However, these are to illustrate the present invention and the present invention is not limited to them.

EXAMPLE

Example 1

Preparation of Tat-hPTHDP Fusion Peptide (KKKKKKKKKGKH) (SEQ ID NO. 10)

(1) Preparation of Tat-hPTHDP Fusion Peptide

The Tat-hPTHDP fusion peptide used in the present invention is a peptide consisting of 12 amino acids having the sequence KKKKKKKKKGKH, and it is synthesized by a solid phase peptide synthesis method using a peptide autosynthesizer (Applied Biosystems Model 431A). 0.25 mmol of parahydroxy methylphenyloxymethyl polystyrene (HMP) resin was introduced in a reaction vessel (38 mL), and Fmoc-amino acid of a carboxy terminal of the peptide to be synthesized was introduced to start synthesis. A cartridge containing 1 mmol of Fmoc-amino acid was arranged in a guideway in the order of from the carboxy terminal amino acid to the amino terminal amino acid. Then metal openings of the cartridge were removed and empty cartridges were laid on the first and the last amino acids.

Before peptide synthesis, a parameter was edited according to the standard scale Fmoc coupling protocol developed in ABI Company, and the peptide synthesis was conducted according to the autosynthesis menu (ABI User's Manual. January, 1992). When using the standard scale Fmoc, deprotection was conducted for 21 minutes using 20% piperidine diluted with N-methylpyrrolidine (NMP), and washing with NMP for 9 minutes and coupling for 71 minutes were conducted. 1-hydroxy-benzotriazole (HOBT) was used for the coupling, and washing with NMP was then conducted for an additional 7 minutes.

(2) Separation and Purification of Tat-hPTHDP Fusion Peptide

After synthesis, the Tat-hPTHDP fusion peptide was separated from the solid support using trifluoroacetic acid (TFA), referring to the ABI Company manual (Introduction to Cleavage Techniques, P6–19(1990)). Specifically, after synthesis, a peptide-attached resin was introduced into a round-bottomed flask and refrigerated, and then 0.75 g of crystal phenol, 0.25 mL of 1,2-ethandithiol (EDT), 0.5 mL of thioanisol, 0.5 mL of distilled water, and 10 mL of TFA were introduced therein and reacted at room temperature for 1 to 2 hours with openings closed. After reaction, the resin and reaction solution was filtered through a sintered glass funnel under low vacuum to separate the resin and peptide solution. The flask and glass funnel were washed with 5~10 mL of dichloromethane (DCM) to mix the solution with the peptide solution, and 50 mL or more of cool diethylether were added to obtain a peptide precipitate. The precipitate was filtered through a funnel under low vacuum, and precipitates gathered on the funnel were dried, melted in 30% acetic acid, and lyophilized. The thus-obtained peptide was purified with HPLC (High Performance Liquid Chromatography). Therein, a C18 analytical column (Pharmacia) was used, and buffer solution A was equilibrated with 10% acetonitrile+0.05% TFA, and the peptide was eluted from buffer solution B using 80% acetonitrile+0.05% TFA. As a result, a highly purified peptide was obtained, and the synthesis yield was approximately 30.5%.

Example 2

Lipolysis Effects Test

In order to measure usefulness of the Tat-hPTHDP prepared in Example 1 as a skin slimming agent, lipolysis effects were tested.

Lipolysis was evaluated using the property of adipocyte for secreting glyreol during lipolysis. In this test, a pre-adipocyte 3T3-L1 cell was used. A 3T3-L1 cell was cultured on a medium treated with 2 µg/mL of insulin, 2 µm of dexamethasone, and 111 µg/mL of isobutylmethylxanthine on a 24-well plate for 48 hours, and it was then cultured on a medium treated with 2 µg/mL of insulin, for 9 days. The thus-cultured 3T3-L1 cell was differentiated into adipocyte to sufficiently accumulate lipids in cells, and then the compound of Chemical Formula 1 was applied thereto to culture for 24 hours.

0.1 mL of buffer solution instead of the sample was used as a blank, and isoproterenol, known to have superior lipolysis effects, was used as a control (Dawn L. Brasaemle et. al Biochem. Biophys. Acta 1483 (2000) 251–262). Then, 50 µl of the culture solution was mixed to react at 37° C. for 24 hours, and absorbency was measured at 540 nm using a spectrophotometer (Beckman DU-7500) to calculate a lipolysis increase rate. The increase rate is as shown in the following Equation, and the results are as shown in Table 1.

Increase Rate (%)=A−B/A×100

A: absorbency at 540 nm without increasing agent
B: absorbency at 540 nm with increasing agent

TABLE 1

| | Concentration (M) | Lipolysis increase rate (%) |
|---|---|---|
| Compound represented by the Chemical Formula 1 | $10^{-8}$ | 8.6 |
| | $10^{-7}$ | 17.4 |
| | $10^{-6}$ | 10.3 |
| | $10^{-5}$ | 43.4 |
| Isoproterenol | $10^{-8}$ | 17.3 |
| | $10^{-7}$ | 34.5 |
| | $10^{-6}$ | 39.0 |
| | $10^{-5}$ | 12.5 |

As a result, the compound represented by the Chemical Formula 1 used in the present invention showed a 43% increase rate at a $10^{-5}$ M concentration, which is lipolysis effects similar to the hormone preparation isoproterenol.

Example 3

Clinical Test for Slimming Effects

In order to examine slimming effects, clinical tests were conducted on 5 healthy adult women of ages 18~46 with local obesity or cellulite inside of a thigh (Method of testing primary irritant substances 38(187): pp1500–1541).

The fusion peptide prepared in Example 1 was prepared in the form of an O/W emulsion and used in the test. A control (O/W emulsion without sample) was coated on one leg, and an O/W emulsion comprising the compound of Chemical Formula 1 of the present invention was coated on the other leg, for one month, and then the thickness of the lipid layer was quantified.

As a result of the test, it can be identified that the compound represented by the Chemical Formula 1 showed an 18% lipid layer decrease, and thus has superior slimming effects.

Example 4

Transdermal Absorption (Penetration into Skin Cells) Test

Penetration of the compound of the Chemical Formula 1 into skin cells is commonly referred to as transdermal absorption, and thus it is commonly called transdermal absorption, herein. The transdermal test was conducted using the fusion peptide prepared in Example 1 (Reference: Lehman P A, Slattery J T, Franz T J. Percutaneous absorption of retinoids: Influence of vehicle, light exposure, and dose, J. Invest Dermatol., 91; 56–61. 1998).

Specifically, skin around the back of a female nude mouse of 8 weeks was cut to a size of 1.7 $cm^2$, and the fusion peptide was applied thereto. After 24 hours, the receptor solution and material absorbed in the skin around the back of mouse were extracted with a transdermal absorption measuring instrument (Franz cell), and quantitatively analyzed using high performance liquid chromatography (HPLC) and liquid chromatography mass (LC mass) to quantify the amount of transdermally-absorbed compound of the Chemical Formula 1 of the present invention. As a result, it can be identified that the compound of the Chemical Formula 1 of the present invention has superior transdermal absorption.

Example 5

Allergy Test of Tat-HPTHDP Fusion Peptide (LLNA)

An experiment using ethanol as a carrier was selected for a safety test of the compound of the Chemical Formula 1 as a cosmetic raw material [Reference: Kimber (1990): Identification of contact allergens using the murinelocal lymph node assay, J. Appl. Toxicol. 10(3); 173–180]. The compound of the Chemical Formula 1 was prepared in 0.5% and 1.0% solutions. Specifically, 50 μl of the solution was applied to both ears of Blab/c mice for 3 days, and then the auricular lymph node was separated from the mice. The lymph nodes were pulverized to a monocell state, and a radioisotope [3H]-methylthymidine was added thereto and cultured for 24 hours. Then, amplification of cells (dpm, disintegrations per minute) was measured using a β-scintillation counter (Beckman LS 6000 TA, USA). As results, the compound of the Chemical Formula of the present invention showed a lower possibility of allergy induction compared to a control.

Example 6

Skin Irritation Test of Tat-hPTHDP Fusion Peptide

In order to test skin irritation of the compound of the Chemical Formula 1, a patch test using Guinea pigs was conducted [Reference: ① Draize, J. H. (!959): Dermal toxicity. Assoc. Food and Drug Officials, US. Appraisal of the safety of chemicals in Food, Drugs, and Cosmetics., pp46–59, Texas State Dept. of Health, Austin, Tex. ② Federal Register (1973): Method of testing primary irritant substances 38(187): pp1500–1541]. The compound represented by the Chemical Formula 1 was prepared in an O/W emulsion of various concentrations. Hairs around the back where the sample was to be coated were removed, and the area was adapted to surroundings for 24 hours in order to minimize skin irritation. Then, a sample coating region was established (1.5 cm×1.5 cm), a sample and gauze were applied thereto, and the coated region was sealed with a thin paper of solid material in order to prevent loss and then fixed with an elastic bandage for 48 hours. At 2 hours and 24 hours after removal of the closed patch (50 hours and 72 hours after patch application), the degree of irritation was determined to indicate an irritation index (PII: primary cutaneous irritation index) and irritation degree, and the results are shown in Table 2.

TABLE 2

| Sample | Concentration (%) | Irritation Index (PII) | Irritation Degree |
|---|---|---|---|
| Control | — | 0.60 | Minute irritation |
| Compound represented by the Chemical Formula 1 | 0.01 | 0.62 | Minute irritation |
| | 0.1 | 0.65 | Minute irritation |
| | 0.5 | 0.71 | Minute irritation |

From Table 2, it can be identified that the compound represented by the Chemical Formula 1 is very safe to skin.

Example 7

Cytotoxicity Test of Tat-hPTHDP Fusion Peptide

In order to identify primary safety of the compound of the Chemical Formula 1 as a cosmetic raw material, V79-4 cells (Chinese hamster, continuous cell line of lung tissue fibroblast) were cultured and an MTT test was conducted to test cytotoxicity for the compound [Reference: Mossaman T. (1983). Rapid calorimetric assay for cellular growth & survival: application to proliferation & cytotoxicity assays. Journal of Immunological Methods 65, 55–63]. As a result, the compound of the Chemical Formula 1 gradually showed very weak toxicity at a concentration of 0.1 (%, w.v) or more, but it showed little toxicity at a concentration of 0.01 or less.

The present invention provides a Tat-hPTHDP fusion peptide wherein a self cell-penetrating Tat peptide having a self penetration signal was bound to a human parathyroid hormone-derived peptide, and a skin slimming agent comprising the same. The slimming agent of the present invention has superior skin absorption, does not cause irritation, and has superior lipolysis effects and durability to the existing hPTHDP, due to the presence of the self cell-penetrating Tat peptide.

What is claimed is:

1. A fusion peptide of Tat-hPTHDP, wherein C-terminal amino acid residue of a self cell-penetrating Tat peptide of HIV Type-1 is bound to N-terminal amino acid residue of human parathyroid hormone-derived peptide (hPTHDP), wherein Tat peptide is selected from the group consisting of amino acid sequences of SEQ ID NOs. 7, 8 and 9, and wherein hPTHDP is selected from the group consisting of amino acid sequences of SEQ ID NOs:1, 2, 3, 4, 5 and 6.

2. A skin slimnniing cosmctic composition comprising the fusion peptide of claim 1 as an active ingredient.

3. The skin slimming cosmetic composition according to claim 2, wherein the fusion peptide of claim 1 is contained in an amount of 0.000001 to 5.0 wt %.

* * * * *

UNITED STATES PATENT AND TRADEMARK OFFICE
CERTIFICATE OF CORRECTION

PATENT NO. : 7,060,673 B2
APPLICATION NO. : 10/296033
DATED : June 13, 2006
INVENTOR(S) : Song et al.

It is certified that error appears in the above-identified patent and that said Letters Patent is hereby corrected as shown below:

<u>Column 14,</u>

Line 3, "slimnniing cosmctic" should read --slimming cosmetic--.

Signed and Sealed this

Nineteenth Day of December, 2006

JON W. DUDAS
*Director of the United States Patent and Trademark Office*

SEQUENCE LISTING

<160> NUMBER OF SEQ ID NOS: 10

<210> SEQ ID NO 1
<211> LENGTH: 34

```
<212> TYPE: PRT
<213> ORGANISM: Artificial Sequence
<220> FEATURE:
<223> OTHER INFORMATION: hPTHDP Sequence

<400> SEQUENCE: 1

Ser Val Ser Glu Ile Gln Leu Met His Asn Leu Gly Lys His Leu Asn
1               5                   10                  15

Ser Met Gln Arg Val Glu Trp Leu Arg Lys Lys Leu Gln Asp Val His
            20                  25                  30

Asn Phe

<210> SEQ ID NO 2
<211> LENGTH: 10
<212> TYPE: PRT
<213> ORGANISM: Artificial Sequence
<220> FEATURE:
<223> OTHER INFORMATION: hPTHDP Sequence

<400> SEQUENCE: 2

Ser Val Ser Glu Ile Gln Leu Met His Asn
1               5                   10

<210> SEQ ID NO 3
<211> LENGTH: 11
<212> TYPE: PRT
<213> ORGANISM: Artificial Sequence
<220> FEATURE:
<223> OTHER INFORMATION: hPTHDP Sequence

<400> SEQUENCE: 3

His Asn Leu Gly Lys His Leu Asn Ser Met Glu
1               5                   10

<210> SEQ ID NO 4
<211> LENGTH: 6
<212> TYPE: PRT
<213> ORGANISM: Artificial Sequence
<220> FEATURE:
<223> OTHER INFORMATION: hPTHDP Sequence

<400> SEQUENCE: 4

Ser Val Ser Glu Ile Gln
1               5

<210> SEQ ID NO 5
<211> LENGTH: 5
<212> TYPE: PRT
<213> ORGANISM: Artificial Sequence
<220> FEATURE:
<223> OTHER INFORMATION: hPTHDP Sequence

<400> SEQUENCE: 5

Gly Lys His Leu Asn
1               5

<210> SEQ ID NO 6
<211> LENGTH: 3
<212> TYPE: PRT
<213> ORGANISM: Artificial Sequence
<220> FEATURE:
<223> OTHER INFORMATION: hPTHDP Sequence

<400> SEQUENCE: 6

Gly Lys His
1
```

```
<210> SEQ ID NO 7
<211> LENGTH: 9
<212> TYPE: PRT
<213> ORGANISM: Artificial Sequence
<220> FEATURE:
<223> OTHER INFORMATION: Tat peptide sequence

<400> SEQUENCE: 7

Arg Lys Lys Arg Arg Gln Arg Arg Arg
 1               5

<210> SEQ ID NO 8
<211> LENGTH: 9
<212> TYPE: PRT
<213> ORGANISM: Artificial Sequence
<220> FEATURE:
<223> OTHER INFORMATION: Tat peptide sequence

<400> SEQUENCE: 8

Lys Lys Lys Lys Lys Lys Lys Lys Lys
 1               5

<210> SEQ ID NO 9
<211> LENGTH: 9
<212> TYPE: PRT
<213> ORGANISM: Artificial Sequence
<220> FEATURE:
<223> OTHER INFORMATION: Tat peptide sequence

<400> SEQUENCE: 9

Arg Arg Arg Arg Arg Arg Arg Arg Arg
 1               5

<210> SEQ ID NO 10
<211> LENGTH: 12
<212> TYPE: PRT
<213> ORGANISM: Artificial Sequence
<220> FEATURE:
<223> OTHER INFORMATION: Tat-hPTHDP sequence

<400> SEQUENCE: 10

Lys Lys Lys Lys Lys Lys Lys Lys Lys Gly Lys His
 1               5                   10
```